United States Patent [19]

Brown et al.

[11] Patent Number: 6,110,696
[45] Date of Patent: *Aug. 29, 2000

[54] ELECTROCHEMICAL ENZYME ASSAY

[75] Inventors: Mary E. Brown, Indianapolis, Ind.; Hans-Joachim Guder, Grunstadt, Germany; John G. R. Hurrell, Carmel, Ind.; Lance S. Kuhn, Fishers, Ind.; Robert J. McEnroe, Noblesville, Ind.; Rebecca W. Muddiman, Indianapolis, Ind.; Mary Luann Ochs, Fishers, Ind.

[73] Assignees: Roche Diagnostics Corporation, Indianapolis, Ind.; Boehringer Mannheim GmbH, Germany

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/494,668

[22] Filed: Jun. 26, 1995

Related U.S. Application Data

[63] Continuation-in-part of application No. 08/113,548, Feb. 27, 1993, Pat. No. 5,427,912.

[51] Int. Cl.[7] .................................................. G01N 33/535
[52] U.S. Cl. ........................... 435/7.6; 204/403; 435/18; 435/23; 435/24; 435/287.2; 435/287.7; 435/287.9; 435/817
[58] Field of Search ................................ 435/7.6, 18, 23, 435/24, 817, 287.2, 287.7, 287.9; 204/403

[56] References Cited

U.S. PATENT DOCUMENTS

| | | | |
|---|---|---|---|
| 4,378,428 | 3/1983 | Farina et al. | 435/7 |
| 4,708,929 | 11/1987 | Henderson | 435/7 |
| 4,785,080 | 11/1988 | Farina et al. | 530/402 |
| 4,830,959 | 5/1989 | McNeil et al. | 435/7 |
| 4,912,041 | 3/1990 | Batchelor et al. | 435/101 |
| 4,950,612 | 8/1990 | Khanna et al. | 436/505 |
| 4,956,274 | 9/1990 | Khanna et al. | 435/7 |
| 4,963,245 | 10/1990 | Weetail | 204/403 |
| 5,032,503 | 7/1991 | Khanna et al. | 435/7.6 |
| 5,037,735 | 8/1991 | Khanna et al. | 435/7.6 |
| 5,106,950 | 4/1992 | Farina et al. | 530/345 |
| 5,120,653 | 6/1992 | Henderson | 435/252.33 |
| 5,124,253 | 6/1992 | Foulds et al. | 435/21 |
| 5,202,233 | 4/1993 | Herrmann et al. | 435/7.4 |
| 5,212,081 | 5/1993 | Coty et al. | 435/188 |
| 5,223,393 | 6/1993 | Khanna et al. | 435/7.6 |
| 5,229,282 | 7/1993 | Yoshioka et al. | 435/177 |
| 5,244,785 | 9/1993 | Loor et al. | 435/7.6 |
| 5,427,912 | 6/1995 | Brown et al. | 435/7.6 |
| 5,444,161 | 8/1995 | Manning et al. | 536/4.1 |

FOREIGN PATENT DOCUMENTS

| | | | |
|---|---|---|---|
| 0 125 139 A2 | 11/1984 | European Pat. Off. | G01N 33/54 |
| 0 150 999 A2 | 8/1985 | European Pat. Off. | G01N 33/53 |
| 0 328 380 A2 | 8/1989 | European Pat. Off. | G01N 27/00 |
| 0350808 | 1/1990 | European Pat. Off. | |
| 0 546 536 A1 | 6/1993 | European Pat. Off. | C12Q 1/00 |
| 86/03837 | 7/1986 | WIPO | G01N 33/53 |
| 86/04926 | 8/1986 | WIPO | C12Q 1/00 |
| 90/13569 | 11/1990 | WIPO | C07K 7/10 |
| 91/16630 | 10/1991 | WIPO | G01N 33/531 |
| 9506115 | 3/1995 | WIPO | |

OTHER PUBLICATIONS

Y. Xu et al., Heterogeneous Enzyme Immunoassay of Alpha–Fetoprotein in Maternal Serum by Flow–Injection Amperometric Detection of 4–Aminophenol, (1990) 1941–1944, Clin. Chem. 36/11.

Thompson et al., Comparison of Methods for Following Alkaline Phosphatase Catalysis: Spectrophotometric versus Amperometric Detection, (1991) 90–95, Analytical Biochemistry 192.

Gil et al., Competitive Heterogeneous Enzyme Immunoassay for Theophylline by Flow–Injection Analysis with Electrochemical Detection of p–Aminophenol, (1990) 662–665, Clin. Chem. 36/4.

Jenkins et al., The Use of Ion Pairing Reagents to Reduce Non–specific Adsorption in a Solid Phase Electrochemical Enzyme Immunoassay, (1990) 99–104, Contributed Article vol. 13 No. 2.

Wright et al., Sequestration Electrochemistry: The Interaction of Chlorpromazine and Human Orosomucoid, (1988) 290–293 Analytical Biochemistry 171.

Jenkins et al., Extending the Detection Limit of Solid–Phase Electrochemical Enzyme Immunoassay to the Attomole Level, (1988) 292–299 Analytical Biochemistry 168.

*Primary Examiner*—David Saunders
*Attorney, Agent, or Firm*—Roche Diagnostics Corporation

[57] ABSTRACT

A diagnostic kit, method, and apparatus for electrochemically determining the presence or concentration of an analyte in a sample. A mixture is formed which includes the sample, an enzyme acceptor polypeptide, an enzyme donor polypeptide, and a labeled substrate. The enzyme donor polypeptide is capable of combining with the enzyme acceptor polypeptide to form an active enzyme complex. The formation of such the active enzyme complex is responsive to the presence or concentration of the analyte in the fluid sample. The active enzyme hydrolyzes the labeled substrate, resulting in the generation of an electroactive label, which can then be oxidized at the surface of an electrode. A current resulting from the oxidation of the electroactive compound can be measured and correlated to the concentration of the analyte in the sample.

31 Claims, 5 Drawing Sheets

(Prior art)

ELECTROCHEMICAL ENZYME ASSAY

CROSS-REFERENCES TO RELATED APPLICATIONS

This is a continuation-in-part of application Ser. No. 08/113,548, filed Aug. 27, 1993, which is now U.S. Pat. No. 5,427,912, issued Jun. 27, 1995.

FIELD OF THE INVENTION

This invention relates generally to the field of electrochemical enzyme assays.

BACKGROUND OF THE INVENTION

Radioimmunoassay was developed in 1960 by Yarlow and Berson as a method for detecting or quantitating antigens or antibodies using radiolabeled reactants. Since the initial studies in 1960, radioimmunoassay (RIA) has developed into a versatile analytical technique, particularly useful in clinical laboratories to quantitate a wide variety of compounds. With RIA, the unknown concentration of an unlabeled antigen is determined by comparing its inhibitory effect on the binding of a radioactively-labeled antigen to an antibody. RIAs do have a number of significant limitations, however, including a limited shelf-life, high cost, and potential environmental harm.

The disadvantages associated with RIAs led to the development of the enzyme immunoassay (EIA), in which the activity of an enzyme is measured to quantitate an analyte. EIAs are subdivided into heterogeneous assays and homogeneous assays. Heterogeneous EIAs require a physical separation of the antibody-bound, labeled analyte from the unbound labeled analyte. With homogeneous EIAs, a separation step is not required. Homogeneous EIAs have been successful commercially because of their speed, simplicity, and automation. The enzymatic activity associated with EIAs is often monitored spectrophotometrically, using a substrate which produces a unique chromophore as a result of an enzymatic reaction.

In addition to using spectrophotometric detection techniques, EIAs have been developed which use electrochemistry to monitor activity of the enzyme label. With electrochemical detection, the active enzyme causes the formation of an active electron mediator or a redox couple from an inactive substrate. The activated mediator or redox couple then shuttles electrons from the enzyme to the electrode or from the electrode to the enzyme. The resulting current can be measured and correlated to analyte level.

Direct electrochemical enzymatic assays (non-immunological) are also known in which the presence or absence of the analyte to be measured causes an electroactive compound to be cleaved from a non-electroactive substrate. The electroactive compound may then be oxidized or reduced and the resulting current measured.

Enzyme complementation immunoassays have also been developed, such as CEDIA® (Cloned Enzyme Donor ImmunoAssay—a registered trademark of the Microgenics Corporation) technology, an example of which is described in U.S. Pat. No. 4,708,929 (issued Nov. 24, 1987), which is hereby incorporated by reference. CEDIA® technology involves the use of enzyme acceptor and enzyme donor polypeptides prepared by recombinant DNA techniques or synthetic peptide synthesis techniques which are capable of spontaneously associating in solution to form an active enzyme complex. This association can be modulated, for example, by conjugating the enzyme donor polypeptide to a member of a specific binding pair, and providing the complimentary member of the specific binding pair elsewhere in the assay. The enzyme donor polypeptide may also be chemically modified to include a specific recognition site that is not a member of a specific binding pair (e.g., a protease site or an esterase site). Accordingly, in its broadest sense, CEDIA® technology allows the formation of an active enzyme complex by the spontaneous association of enzyme acceptor and enzyme donor polypeptides to be dependent on the presence or concentration of an analyte of interest. The amount of enzymatic activity is then monitored spectrophotometrically.

One embodiment of CEDIA® technology is shown in FIG. 1. Analyte analog 1 is covalently attached to enzyme donor polypeptide 2 to form enzyme donor polypeptide conjugate 3. Analyte-specific antibody 4 can be used to inhibit reassembly of enzyme donor polypeptide conjugate 3 with enzyme acceptor polypeptide 6. When a sample containing analyte 8 is introduced, analyte 8 and enzyme donor polypeptide conjugate 3 compete for binding to antibody 4. As the amount of analyte 8 increases, less enzyme donor polypeptide conjugate 3 binds to antibody 4 and more active enzyme 10 is formed. Active enzyme 10 hydrolyzes enzyme substrate 11 (e.g., chlorophenol-red-$\beta$-D-galactopyranose (CPRG)), which then undergoes a color change and is monitored spectrophotometrically.

SUMMARY OF THE INVENTION

The present invention is based on the novel combination of CEDIA® technology (i.e., the modulation of enzyme activity in response to the presence or concentration of an analyte) with electrochemical detection of the resulting enzyme activity in order to determine the presence or concentration of the analyte. The advantages that result from this combination include the speed and simplicity of a homogeneous EIA and the simplicity, enhanced analyte sensitivity, small sample volume requirement, and adaptability to sensor formats associated with electrochemical measurement of enzyme activity.

The assay components include an enzyme acceptor polypeptide (EA), an enzyme donor polypeptide (ED), a substrate for enzymatic reaction, and a label which is bound to the substrate and is preferably nonelectroactive until cleaved from the substrate. ED is capable of combining with EA to form an active enzyme complex, the formation of the active enzyme complex being responsive to the presence or concentration of an analyte in a sample, The sample containing the analyte is mixed with a first reagent (EA reagent) which includes EA. This mixture is then mixed with a second reagent (ED reagent) which includes ED and the labeled substrate. The enzyme activity resulting from the combination of EA and ED is responsive to the presence or concentration of the analyte. The active enzyme then cleaves the label from the substrate, which may be detected electrochemically. The current measured from the oxidation of the label may then be correlated to the concentration of the analyte in the sample.

DESCRIPTION OF THE PREFERRED EMBODIMENTS

Figure 1:
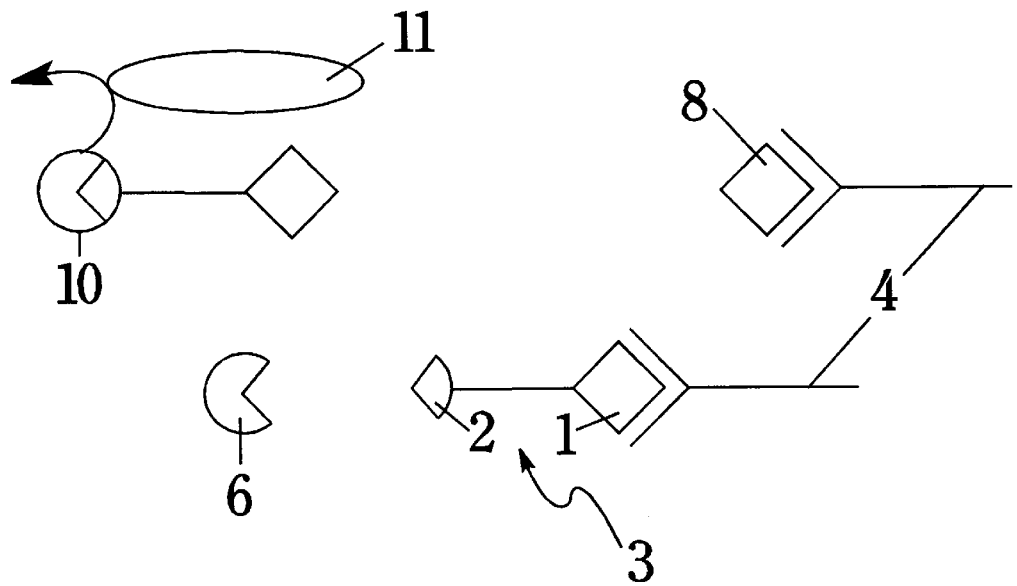
FIG. 1 is a block diagram of the assay components of one embodiment of CEDIA® technology.

The present invention includes EA and ED which are capable of spontaneously combining to form an active enzyme complex, wherein such combination is responsive to the presence or concentration of an analyte in a fluid sample. For example, ED may be modified so that ED spontaneously combines with EA unless hindered by the presence or concentration of an analyte. Such a modification may be, for example, conjugation of ED to a member of a specific binding pair wherein the conjugate is capable of spontaneously combining with EA to generate enzyme activity. The member of the specific binding pair conjugated to ED may be an analyte or an analyte analog, or a complimentary member of a specific binding pair (e.g., antibody) which binds to the analyte.

The EA and ED may be contained in reagents which include components necessary for modulating enzyme activity in response to the presence or concentration of an analyte. For example, the reagents may include antibodies which bind specifically to the analyte and to analyte conjugated to ED, thereby hindering the spontaneous association of EA and ED. The reagents may also include other specific binding proteins or substances which bind to analyte and analyte conjugated to ED, antibodies to analyte which compete with antibodies or antibody fragments bound to ED for binding to analyte, antibodies to the specific binding proteins or antibodies which increase the modulation of the association of EA and ED in response to analyte, or some combination of reagents which modulate the generation of enzyme activity in response to the presence or concentration of analyte. The EA and ED reagents may be provided as mixtures of several active components, with other inactive components (e.g., buffer salts and stabilizing proteins) added to the assay solution in various orders, with or without incubations between the various additions.

The present invention also includes a substrate, which bears an electroactive label, and an electrochemical cell. When EA, ED, and a sample containing an analyte of interest are mixed, enzyme activity is generated in response to the presence or concentration of the analyte in the sample mixture. The enzyme activity acts on the labeled substrate to free label into the reaction mixture. The free label is then measured electrochemically by means known in the art. For example, the electrodes of the electrochemical cell may be maintained at a potential sufficient to cause oxidation of the freed label but not the label still bound to substrate. The current produced from the oxidation of the free label may then be measured and correlated to the presence or amount of analyte in the sample mixture.

Analytes

The presence or concentration of both high and low molecular weight analytes may be determined using the present invention. Examples of such high molecular weight analytes include ferritin, hCG, carcinoembryonic antigen, human T-cell leukemia virus, insulin, α-fetoprotein, rubella virus, herpesvirus, cytomegalovirus, follicle stimulating hormone, thyroid stimulating hormone, leutinizing hormone, hepatitis virus, chorionic gonadotropin, estrogen receptor, thyroid stimulating hormone receptor, poliovirus receptor, insulin transport protein, protein A, concanavalin A lectin, wheat germ agglutinin lectin, secretory protein, cholera toxin, and avidin.

Examples of low molecular weight analytes include theophylline, vitamin $B_{12}$, folate, estriol, digoxin, thyroxine, propranolol, methotrexate, phencyclidine, methadone, morphine, diazepam, oxazepam, quinidine, propoxyphen, N-acetylprocainamide, secobarbital, tobramycin, gentamicin, amphetamine, benzoyl ecogonine, phenytoin, procainamide, lidocaine, carbamazepine, primidene, valproic acid, phenobarbital, ethosuximide, and biotin.

Enzyme Substrates

Figure 3:
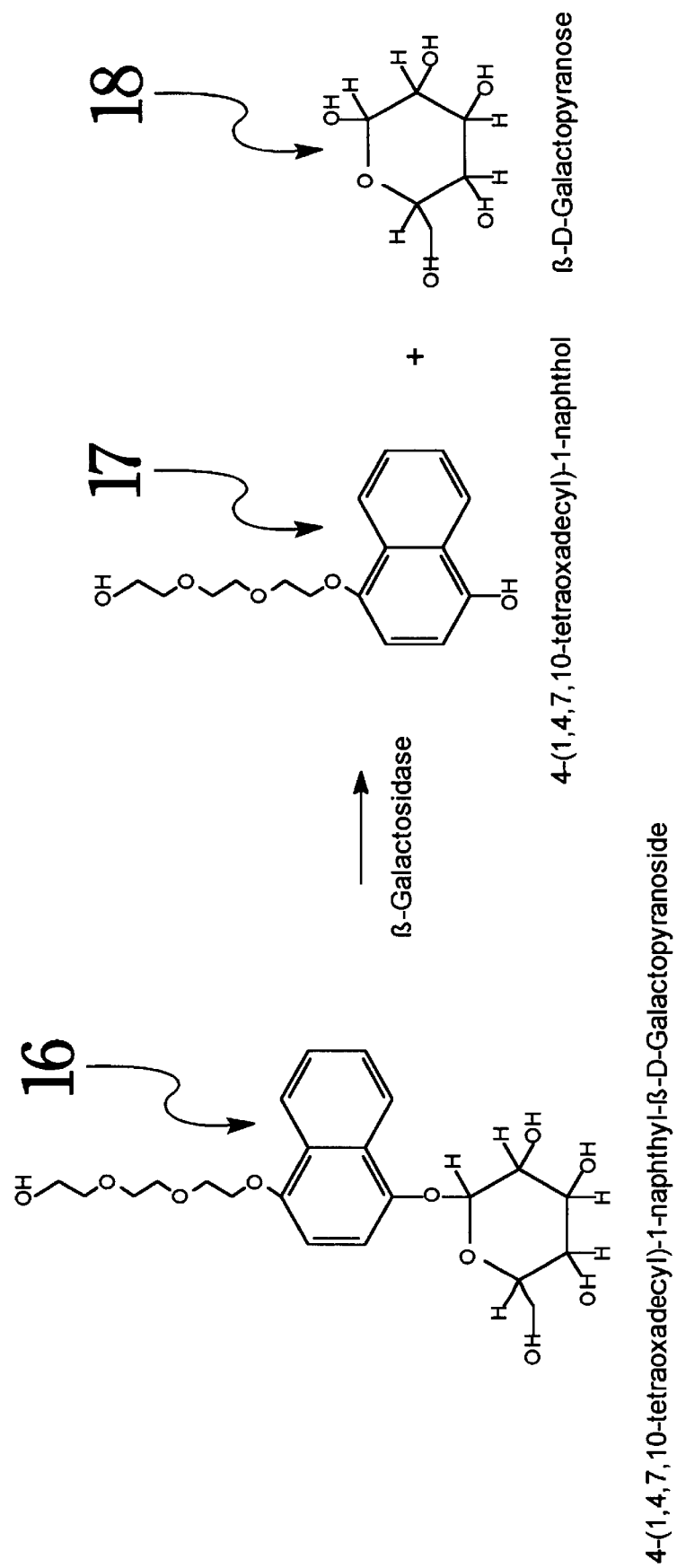
FIG. 3 is a representation of the biochemical events of one embodiment of the present invention, using the example of 4-(1,4,7,10-tetraoxadecyl)-1-naphthyl-β-D-galactopyranoside as a labeled substrate.

In the present invention, enzyme activity is monitored electrochemically by using an enzyme substrate which is covalently linked to a label. An example of such a labeled substrate is shown in FIG. 3. labeled substrate 16 (4-(1,4,7,10-tetraoxadecyl)-1-naphthyl-β-D-galactopyranoside) is nonelectroactive until enzymatic hydrolysis cleaves electroactive label 17 (4-(1,4,7,10-tetraoxadecyl)-1-naphthol) from substrate 18 (β-D-galactopyranose). Label 17 (4-(1,4,7,10-tetraoxadecyl)-1-naphthol) is then oxidized at the surface of an electrode, resulting in a current which may be measured.

The β-galactosidase enzyme is especially suitable for use with the present invention. Use of this enzyme results in smaller background signals and therefore greater analyte sensitivity, since there is no natural β-galactosidase activity in human blood. β-galactosidase substrates that may be used with the present invention will now be described. (If enzymes other than β-galactosidase are used in the preparation of enzyme acceptor fragment EA and enzyme donor polypeptide conjugate ED, as described above, other substrates become necessary.)

In accordance with the present invention, the labeled substrate should be soluble in aqueous medium and is preferably electrochemically inactive when scanned in the potential range of −0.6 V (volts) to +1.0 V vs. Ag/AgCl. When cleaved from the substrate, the label should be electrochemically active in this same potential range. Preferences for the cleaved label include a near zero redox potential (0.0V<E°<0.5V vs. Ag/AgCl), electrochemical reversibility, and aqueous solubility.

Electrochemical characteristics of some β-galactosidase labeled substrates and their cleaved labels are provided in Table 1.

TABLE 1

Examples of β-galactosidase labeled substrates and their cleaved labels

| Compound | Elec. Active? | $E_{ox}$ vs. Ag/AgCl | Reversible? | Solubility |
|---|---|---|---|---|
| resorufin-β-D-galactopyranoside | yes | −0.100 V | yes | soluble |
| resorufin (cleaved) | yes | −0.100 V | yes | soluble |
| 4-methoxy-1-naphthyl-β-D-galactopyranoside | yes | −0.10 V, +1.00 V | quasi, no | slightly |
| 4-methoxy-1-naphthol (cleaved) | yes | −0.10 V, +0.20 V | quasi, no | no |
| p-aminophenyl-β-D-galactopyranoside | no | — | — | soluble |
| p-aminophenol (cleaved) | yes | +0.18 V | yes | soluble |
| 4-(1,4,7,10-tetraoxadecyl)-1-naphthyl-β-D-galactopyranoside | yes | +0.05 V, +1.00 V | no,no | soluble |
| 4-(1,4,7,10-tetraoxadecyl)-1-naphthol (cleaved) | yes | +0.38 V | no | soluble |

Although it is preferable for the labeled substrate to be electrochemically inactive and the cleaved label electrochemically active, both may be electrochemically active so long as they are active at potentials at least 118 millivolts (mV) apart. (For example, labeled substrate 4-(1,4,7,10-tetraoxadecyl)-1-naphthyl-β-D-galactopyranoside is electrochemically active at +0.05 V and +1.00 V. but cleaved label 4-(1,4,7,10-tetraoxadecyl)-1-naphthol is only electroactive at +0.38 V.)

Referring to Table 1, labeled substrate 4-(1,4,7,10-tetraoxadecyl)-1-naphthyl-β-D-galactopyranoside is the preferred labeled substrate for the present invention because of its aqueous solubility, which facilitates reagent formulation. Labeled substrates p-aminophenyl-β-D-galactopyranoside and 4-methoxy-1-naphthyl-β-D-galactopyranoside also work well but are not preferred since 4-methoxy-1-naphthyl-β-D-galactopyranoside is less soluble than 4-(1,4,7,10-tetraoxadecyl)-1-naphthyl-β-D-galactopyranoside and p-aminophenyl-β-D-galactopyranoside has slower kinetics (i.e., the label is released more slowly under conditions of enzymatic hydrolysis) than 4-(1,4,7,10-tetraoxadecyl)-1-naphthyl-β-D-galactopyranoside. Labeled substrate resorufin-β-D-galactopyranoside is an example of a β-galactosidase labeled substrate that does not work with the present invention, since it is electrochemically active at the measurement potential before and after cleavage.

Other labeled substrates which may be used to monitor enzyme activity include 4-chloro-1-naphthyl-β-D-galactopyranoside, 4-propoxy-1-naphthyl-β-D-galactopyranoside, 4-isopropoxy-1-naphthyl-β-D-galactopyranoside, 4-benzyloxy-1-naphthyl-β-D-galactopyranoside, and 4-trifluoroethoxy-1-naphthyl-β-D-galactopyranoside. Preparation of these labeled substrates and the labeled substrate 4-methoxy-1-naphthyl-β-D-galactopyranoside (described above) is disclosed in U.S. Pat. No. 5,202,233 (issued Apr. 13, 1993), the disclosure of which is hereby incorporated by reference.

Other commercially-available labeled substrates which also may be used in accordance with the present invention include p-nitrophenyl-β-D-galactopyranoside, chlorophenol red-β-D-galactopyranoside (CPRG), o-nitrophenyl-β-D-galactopyranoside, umbelliferyl-β-D-galactopyranoside, o-methoxy-p-nitrophenyl-β-D-galactopyranoside, 3,4-dinitrophenyl-β-D-galactopyranoside, m-cyano-p-nitrophenyl-β-D-galactopyranoside, 4-nitrosalicylaldehyde-β-D-galactopyranoside, and 4-metbyl-umbelliferyl-β-D-galactopyranoside.

The synthesis of 4-(1,4,7,10-tetraoxadecyl)-1-naphthol, disclosed by Goeltner et al., Liebigs Ann. Chem., 1991, 1085–1089, is as follows: 2.0 grams (g) (12.5 millimoles (mmol)) naphthohydroquinone is added to 80 milliliters (ml) triethylene glycol to yield 3.4 g (92%) of a violet oil which, after column chromatography ($SO_2$-saturated ethyl acetate), hardens into pink needles with a melting point of 70° C. The crude product, 4-(1,4,7,10-tetraoxadecyl)-1-naphthol, is then attached to β-D-galactopyranose to form labeled substrate 4-(1,4,7,10-tetraoxadecyl)-1-naphthyl-β-D-galactopyranoside as described below in the synthesis of 4-methoxy-1-naphthyl-β-D-galactopyranoside, except that 4-(1,4,7,10-tetraoxadecyl)-1-naphthol is used in place of 4-methoxy-1-naphthol.

Methods of synthesis for p-aminophenyl-β-D-galactopyranoside and p-nitrophenyl-β-D-galactopyranoside are publicly known.

Electrochemical Cells

Performing an assay in accordance with the present invention involves making an electrochemical measurement. One example of an electrochemical cell that can be used to make such an electrochemical measurement will now be described.

Figure 4:
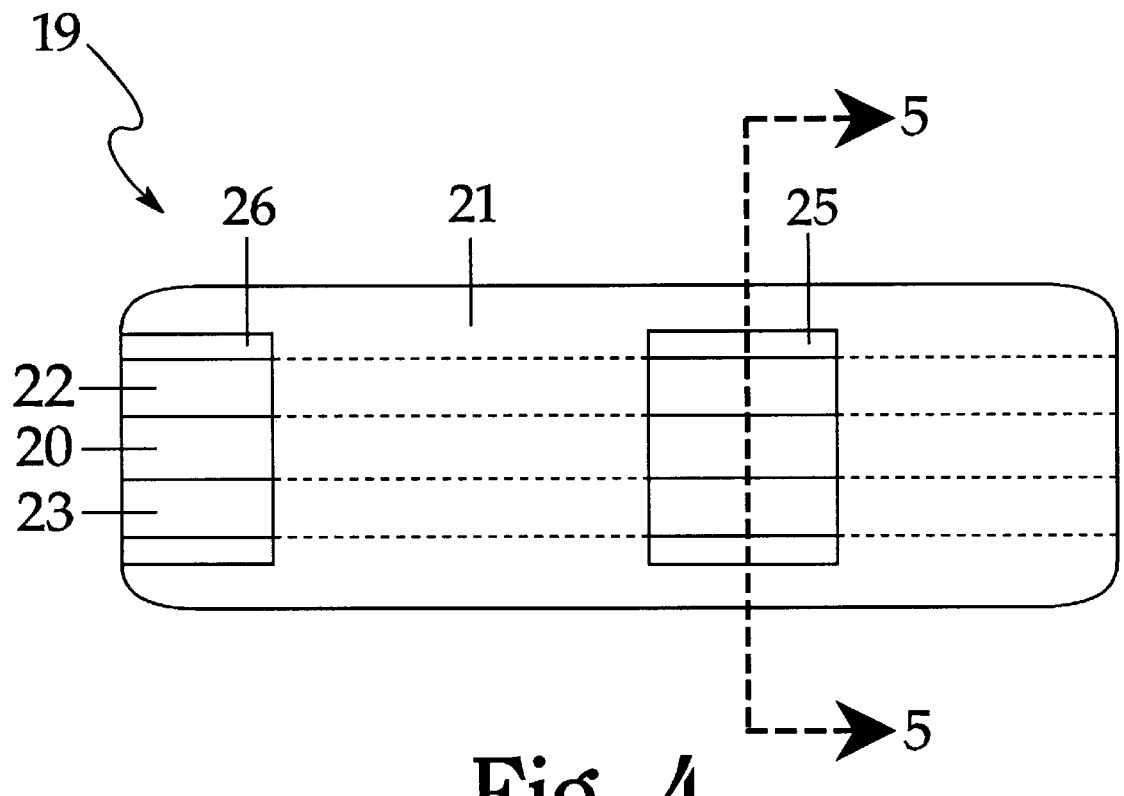
FIG. 4 is a schematic top view of an embodiment of an electrocell used with the present invention.
Figure 5:
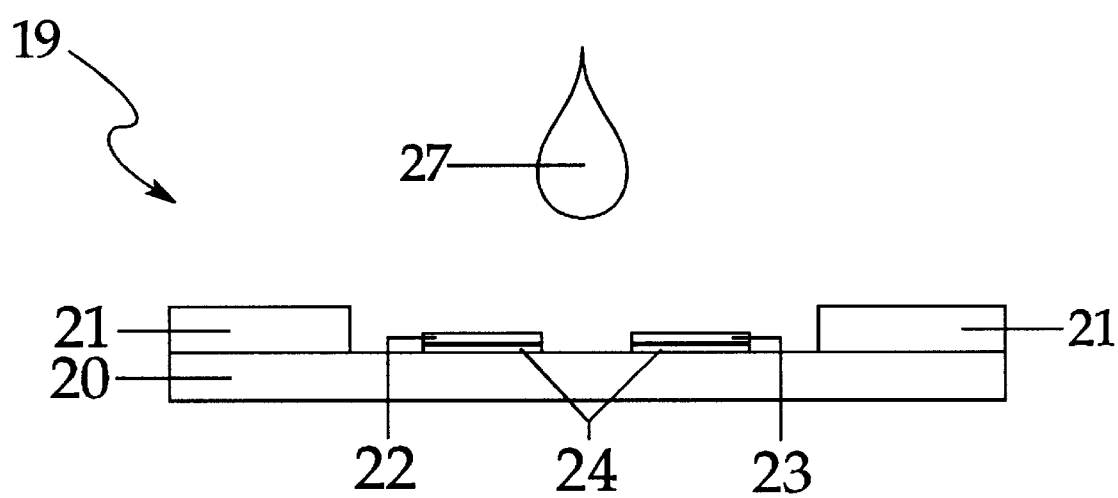
FIG. 5 is a schematic cross-sectional view of FIG. 4 taken along line 5—5 of FIG. 4.

Reference is now made to FIGS. 4 & 5. Electrocell (e-cell) 19 has a first insulating substrate 20, which is about 360 microns thick and made of polyester. Other substrates and thicknesses could also be used. Typically, plastics such as vinyl polymers and polyimides provide the electrical and structural properties which are desired. First electrode 22 and second electrode 23 are each about 0.1 micron thick, made of palladium, and are affixed to first insulating substrate 20 by the use of hot melt adhesive (not shown). In addition to palladium, other electrically conducting materials may be used for electrodes 22 and 23, including platinum, gold, silver, carbon, titanium, and copper. Noble metals are preferred because they provide a more constant, reproducible electrode surface area. Palladium is particularly preferred because it is one of the more difficult noble metals to oxidize. Silver is not preferred because it is more readily oxidized by air than the other noble metals listed above. Electrodes 22 and 23 should be sufficiently separated so that the electrochemical events at one electrode do not interfere with the electrochemical events at the other electrode.

Electrodes 22 and 23 are deposited on a backing of insulator material 24, a polyimide, to reduce the possibility of tearing the electrode before it is affixed to substrate 20. Backing 24 is about 25 microns thick. The electrode and polyimide combination is commercially vailable from Courtaulds Performance Films in California. Electrodes 22 and 23 extend from one end of substrate 20 to the other end in parallel configuration. The distance between electrodes 22 and 23 is about 1.2 mm (millimeters).

Second insulating substrate 21 is fixed on top of first insulating substrate 20 and electrodes 22 and 23 by the use of hot melt adhesive (not shown). Substrate 21 is about 250 microns thick, made of polyester, and includes sample window 25 which exposes at least a portion of electrodes 22 and 23. Sample window 25 is 4 mm by 6 mm and electrodes 22 and 23 are each 1.5 mm in width. Therefore, a surface area of about 6 mm$^2$ is exposed for each of the two electrodes. Substrate 21 also has cutout portion 26 at one end to allow an electrical connection between the electrodes and a power source (not shown) and a current measuring meter (not shown). As discussed above with substrate 20, other substrates and thicknesses may be used for substrate 21.

In the electrocell embodiment described above, the first and second electrodes described are working and counter electrodes. This embodiment has the advantage of being easy to manufacture. Although the described embodiment only has the reduced form of the label attached to the substrate, the oxidized form of the label (e.g., 4-(1,4,7,10-tetraoxadecyl)-1-naphthal) should also preferably be present in the reagent in high concentration (at least twice the concentration of the amount of the reduced form of the cleaved label (e.g., 4-(1,4,7,10-tetraoxadecyl)-1-naphthol) expected to be produced by the assay) when using the working/counter electrode design described above. Since the oxidation of the label is being measured, the oxidation and not the reduction should be the current-limiting event. Having an excess of the reduced form of the label helps ensure that the reduction of the label is not current-limiting.

Other electrocell configurations are possible. For example, a two electrode electrocell using a reference electrode (e.g., Ag/AgCl) rather than a counter electrode or a three electrode electrocell using working, counter and reference electrodes are possible. The preferred embodiment of the referenced two or three electrode electrocells would not need the oxidized form of the label present in the reagent.

EXAMPLE 1

Theophylline Assay

The Theophylline System Pack (a CEDIA® assay, commercially available from Boehringer Mannheim Corporation) is an EIA for the quantitative determination of theophylline in serum or plasma. The Theophylline System Pack was modified and optimized to allow measurements to be performed in accordance with the present invention. The contents of the Theophylline System Pack referred to above will now be described.

The enzyme used in the Theophylline System Pack is split into two inactive fragments, EA and ED, through the use of recombinant DNA technology. EA is a relatively large polypeptide containing approximately 95% of the native β-galactosidase enzyme protein sequence. ED is a small polypeptide containing approximately 5% of the native β-galactosidase enzyme. EA can spontaneously recombine with ED to form a catalytically active enzyme. The analyte analog is covalently bound to ED in a way that does not interfere with reassociation of the enzyme fragments.

The Theophylline System Pack includes four primary components: (i) EA reagent (lyophilized), (ii) EA reconstitution buffer, (iii) ED reagent (lyophilized), and (iv) ED reconstitution buffer. The EA reagent (lyophilized) includes the EA fragment of the enzyme, monoclonal anti-theophylline antibody, buffer salts, surfactants, carrier proteins, and preservative. A vial of the EA reagent is reconstituted with 20 ml (milliliters) of EA reconstitution buffer. The EA reconstitution buffer includes 3-(N-morpholino)propanesulfonic acid buffer solution (MOPS), stabilizers, and preservative.

The ED reagent (lyophilized) includes the ED fragment of the enzyme, buffer, chlorophenol-red-β-D-galactopyranoside (CPRAG), surfactants, stabilizer, secondary antibody, and preservative. A vial of the ED reagent is reconstituted with 16 ml of ED reconstitution buffer, which is similar in composition to the EA reconstitution buffer.

Figure 2:
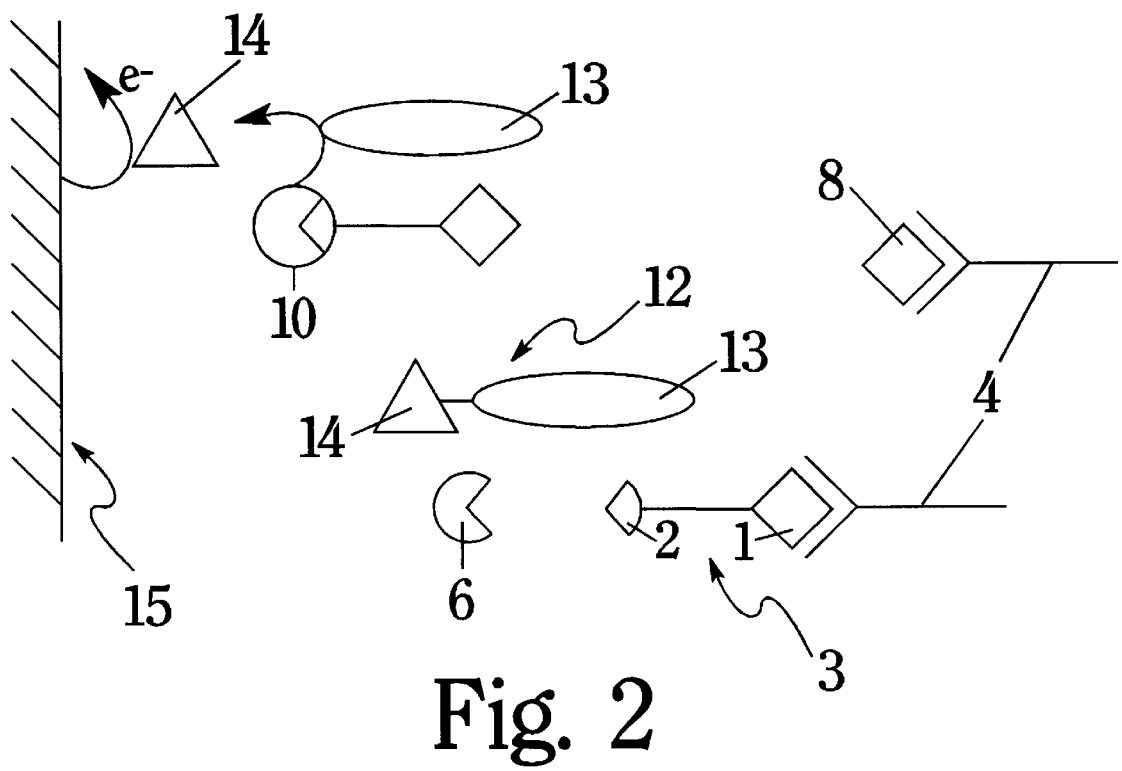
FIG. 2 is a block diagram of one embodiment of the present invention.

The Theophylline System Pack described above may be modified for use in the present invention. Referring to FIG. 2, analyte analog 1, enzyme donor polypeptide 2, ED 3, antibody 4, EA 6, sample analyte 8, and active enzyme 10 all have the same function as in the CEDIA® assay described in FIG. 1. However, labeled substrate 12 is made by covalently linking label 14 to substrate 13 in such a way that label 14 is nonelectroactive at the measurement potential until cleaved from substrate 13 by enzymatic hydrolysis. Label 14 may then be oxidized at the surface of electrode 15 to produce a current which may be correlated to the detection or measurement of analyte 8 present in the sample being analyzed. The present invention allows an assay to be performed on a sample of about 25 μl (microliters), whereas the Theophylline System Pack assay requires a sample volume of about 250 μl.

The Theophylline System Pack was modified as described in Tables 2 through 5, which identify the components, concentrations, and functions of the components in accordance with the present invention.

TABLE 2

Theophylline System Pack modifications - ED reagent

| Modified ED Reagent | Concentration | Function |
|---|---|---|
| Potassium Phosphate, dibasic | 80.000 mM | buffer |
| Fragmented Bovine Serum Albumin (BSA) | 2.000 mg (milligrams)/ml | protects viability of antibody and enzymes |
| Heat inactivated goat anti-mouse serum (GAMS) | 47.600 ml/l (liter) | provides steric hindrance to antibody |
| Labeled substrate (enzyme substrate) (see below) | | provides means for monitoring enzyme activity |
| ED-theophylline conjugate | 1.613 ml/l | enzyme donor fragment - coupled to theophylline |

TABLE 3

Theophylline System Pack modifications - ED reconstitution buffer

| Modified ED Reconstitution Buffer | Concentration | Function |
|---|---|---|
| Potassium Phosphate, dibasic | 0.0205 M (molar) | buffer |
| Potassium Phosphate, monobasic | 0.0295 M | buffer |
| Sodium Chloride (NaCl) | 1.00 M | prevents salting out of antibodies |
| Tween 20 (10% aqueous solution) | 0.020% by volume | surfactant |

TABLE 4

Theophylline System Pack modifications - EA reagent

| Modified EA Reagent | Concentration | Function |
|---|---|---|
| Potassium Phosphate, dibasic | 4.000 mM (millimolar) | buffer |
| EA | 203.520 U (Units)/ml | enzyme acceptor fragment |
| Theophylline monoclonal antibody | 25 µg (micrograms)/ml | theophylline antibody |
| Theophylline high calibrator | 40 mg/l | shifts reaction into linear range of curve |

TABLE 5

Theophylline System Pack modification - EA reconstitution buffer

| Modified EA Reconstitution Buffer | Concentration | Function |
|---|---|---|
| Potassium Phosphate, dibasic | 0.0205 M | buffer |
| Potassium Phosphate, monobasic | 0.0295 M | buffer |
| Sodium Chloride (NaCl) | 1.00 M | prevents salting out of antibodies |
| Magnesium Acetate | 0.0078 M | provides source of $Mg^{2+}$ for enzymatic reaction |
| Tween 20 (10% aqueous solution) | 0.020% | surfactant |

The EA and ED reagents and reconstitution buffers described above were prepared as follows. EA reagent: a bulk potassium phosphate buffer with a concentration of 4.000 mM was prepared in deionized, distilled water. (Since an electrochemical measurement is being made in the present invention, it is important that the buffer is electrochemically inactive at the measurement potential.) The pH was adjusted to 7.1 at 25° C. by addition of 1N (normal) HCl (hydrochloric acid). The buffer was then filtered through sterile 0.2 µm (micrometer) cellulose acetate. The enzyme acceptor fragment (EA) was cut using sodium sulfate and the EA concentration was titered before it was added to the bulk buffer at about 200 U/ml (β-galactosidase units defined by its reaction with chlorophenol-red-β-D-galactopyranoside (CPRG), based on the extinction coefficient of the cleaved substrate). Theophylline monoclonal antibody was added to the reagent at a concentration of about 25 µg/ml. Excess theophylline was then added to the reagent at a concentration of 40 mg/l. The excess theophylline increases the linearity of the system by shifting the low end of the calibration curve into the linear range. The reagent was then assayed versus a reference reagent and adjusted to achieve appropriate activity (a titration to ensure there is enough β-galactosidase, theophylline, and theophylline monoclonal antibody to measure the highest concentration of theophylline to be detected by the assay). The reagent was then filtered through a 0.2 µm cellulose acetate filter and 4 ml was lyophilized in a glass bottle.

ED reagent: a bulk potassium phosphate buffer with a concentration of 80.000 mM was prepared in deionized, distilled water. (As stated above, it is important that the buffer is electrochemically inactive at the measurement potential.) Pepsin-digested BSA was then added to the buffer at a concentration of 2.0 mg/ml. The addition of BSA (protein fragments) to the ED reagent reduces hydrolysis of the enzyme donor polypeptide conjugate from proteases in the fluid sample (i.e., the BSA enhances stability of the antibody and ED—the resulting hydrophobic interactions maintain the conformation of proteins). The synthesis of pepsin-digested BSA is described in example 2, column 7, lines 26–40 (using the 60 minute incubation period) of U.S. Pat. No. 5,212,081 (Coty et al., issued May 18, 1993), the disclosure of which is hereby incorporated by reference. The pH was then adjusted to 7.1 at 25° C. Heat-inactivated goat anti-mouse serum (GAMS) was then added to achieve a protein concentration of 10 g (grams)/l. GAMS contains a second antibody, capable of binding to theophylline monoclonal antibody, that helps reduce background signal by providing extra steric hindrance to ensure the ED fragment does not complement with the EA fragment when ED is bound to the monoclonal theophylline antibody. The reagent was then filtered through a 0.2 µm cellulose acetate filter. Finally, the enzyme donor polypeptide conjugate (ED) was added. The reagent was then assayed versus a reference reagent, which contained the ED reagent components in known concentrations. 4 ml of the ED reagent was then lyophilized in a glass bottle.

EA reconstitution buffer: a potassium phosphate buffer was prepared at a concentration of 0.05 M. Sodium chloride was added until the solution was 1.0 M in sodium chloride, and magnesium acetate was added until its concentration was 0.0078 M. A small amount of Tween 20 detergent (see Table 5 above) was then added. The ED reconstitution buffer was prepared in the same manner, except that magnesium acetate was not added.

Preparation of enzyme acceptor fragment EA and enzyme donor polypeptide conjugate ED by recombinant DNA methods in accordance with the present, invention is fully described in U.S. Pat. No. 4,708,929, incorporated by reference above.

An assay for theophylline was then performed as follows. A labeled substrate stock solution was prepared which included 0.307 molar (M) 4-methoxy-1-naphthyl-β-D-galactopyranoside in DMSO. 20 ml of the EA reconstitution buffer was added to the lyophilized EA reagent. 15.877 ml of the ED reconstitution buffer and 0.123 ml of the labeled substrate stock solution was added to the lyophilized ED reagent. 293 µl (microliters) of the reconstituted EA reagent was dispensed into an incubated tube. 23 µl of a serum sample was then added to the reconstituted EA reagent and the solution was briefly and gently mixed. The reconstituted EA reagent/sample mixture was allowed to incubate at a temperature of 35–37° C. for 4 minutes and 36 seconds. 220 µl of the reconstituted ED reagent was then added to the reconstituted EA reagent/sample mixture and the solution was briefly and gently mixed. The full mixture was then allowed to incubate at a temperature of 35–37° C. for 19 minutes and 16 seconds.

After the final incubation, about 20 µl of the full mixture was applied to the sample window of the electrocell described above and shown in FIGS. 4 and 5. The electrodes were electrically connected to a power source and a current measuring meter. When palladium first and second electrodes are utilized in the electrocell, a potential difference of 450 mV (millivolts) was applied between the two electrodes. (Potential differences less than 450 mV are not preferred because non-diffusion-limited currents are possible. Potential differences greater than 450 mV are not preferred because unnecessary oxidation of interfering compounds in the sample is possible.) The current generated was measured for about 5 seconds. The amount of current measured 3 seconds after application of the potential difference was then compared to a calibration curve and theophylline concentration in the serum sample was determined. (Current reading times of less than 3 seconds are not preferred because less precise measurements may result. Current reading times of greater than 3 seconds are not preferred because smaller currents and lower sensitivity may result.) Minimal background signals were observed, since there is no β-galactosidase activity in human blood, the uncombined EA and ED fragments are not electrochemically active, and because there are few endogenous electrochemically active compounds in blood. As a result, practice of the present invention results in enhanced analyte sensitivity.

EXAMPLE 2

Theophylline Assay Using a Dry-Chemistry Immunosensor

In addition to using the aqueous reagents and electrocell described above, the present invention could also be practiced by using a dry-chemistry immunosensor. Two examples of such an immunosensor will now be described.

Figure 6:
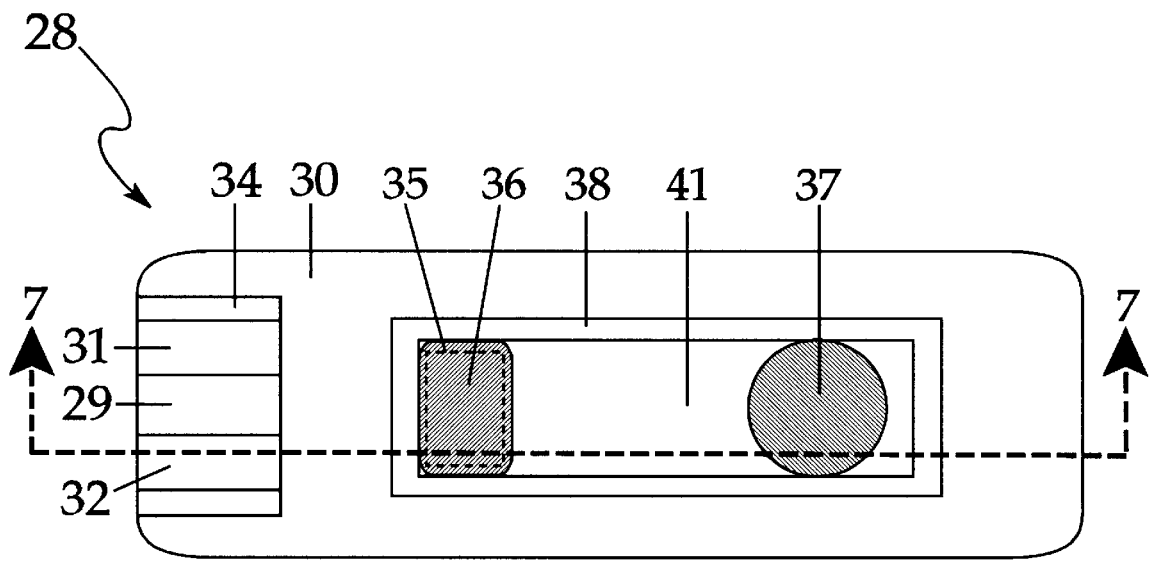
FIG. 6 is a schematic top view of an embodiment of an immunosensor of the present invention, excluding the fourth insulating substrate.
Figure 7:
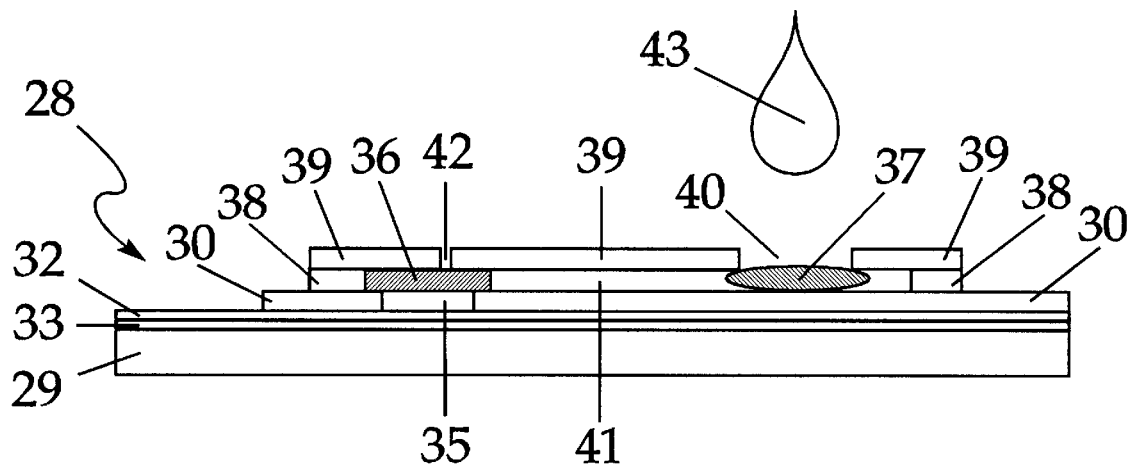
FIG. 7 is a schematic cross-sectional view of FIG. 6 taken along line 7—7 of FIG. 6, including the fourth insulating substrate.

Reference is now made to immunosensor 28 shown in FIGS. 6 & 7. First insulating substrate 29, first electrode 31, second electrode 32, and insulator material 33 are all similar in composition and function to first insulating substrate 20, first electrode 22, second electrode 23, and insulator material 24 described above in FIGS. 4 & 5. (A two-electrode electrocell and a three-electrode electrocell, utilizing working and reference electrodes, are also possible, as described above for electrocell 19.) Immunosensor 28 also has second insulating substrate 30, fixed on top of first insulating substrate 29 and electrodes 31 and 32 by the use of hot melt adhesive (not shown). Substrate 30 is about 250 microns thick, made of polyester, and includes window 35 which exposes at least a portion of electrodes 31 and 32. Substrate 30 also has cutout portion 34 at one end to allow an electrical connection between the electrodes and a power source (not shown) and a current measuring meter (not shown).

Immunosensor 28 also has a polyester mesh 36. Polyester mesh 36 may be any porous substrate that has sufficient porosity to allow passage of a whole blood sample. Examples of porous substrates that may be used include meshes, films, soluble polymers, and membranes. Polyester mesh 36 is impregnated with the ED reagent (described above) by dispensing about 5 μl of the ED reagent directly onto mesh 36. Mesh 36 is then dried by heating at about 50° C. for about 15 minutes. After the reagent has dried, mesh 36 is affixed above window 35 in second insulating substrate 30 as shown in FIG. 7.

About 6 μl of EA reagent 37 (described above) is dispensed directly onto second insulating substrate 30 as shown in FIG. 7. Third insulating substrate 38 is placed over second insulating substrate 30. Third insulating substrate 38 is a thin insulating substrate which preferably has adhesive material on each side to hold it in place. Third insulating substrate 38 includes cutout portion 41. Fourth insulating substrate 39 (not shown in FIG. 6) is placed over third insulating substrate 38, such that a capillary space is formed within cutout portion 41 of third insulating substrate 38 which allows capillary flow from EA reagent 37 to polyester mesh 36 (which is impregnated with ED reagent). Fourth insulating substrate 39 is about 250 microns thick, made of polyester, and includes sample window 40 (not shown in FIG. 6) which exposes EA reagent 37, and vent hole 42 (not shown in FIG. 6).

Immunosensor 28 may be used to determine the concentration of an analyte in a whole blood sample by the following method. Whole blood sample 43 (about 20 μl) is applied to sample window 40 of immunosensor 28. A mixture of EA reagent 37 and blood sample 43 is formed, which is drawn to polyester mesh 36 by capillary action caused by cutout portion 41 and vent 42. The ED reagent, impregnated in mesh 36, then becomes part of the mixture. The mixture of EA reagent 37, ED reagent, and blood sample 49 then settles on electrodes 31 and 32 through window 35 of second insulating substrate 30. After an incubation period of about 20 minutes, a potential difference of 450 mV is applied between electrodes 31 and 32 (palladium first and second electrodes, as described above, electrically connected to a power source and a current, measuring meter). The current generated is measured about 5 seconds. The amount of current measured 3 seconds after application of the potential difference is then compared to a calibration curve and analyte concentration in the whole blood sample is determined.

EXAMPLE 3

Theophylline Assay Using a Dry-Chemistry Immunosensor

Another example of a dry chemistry immunosensor that can be used to practice the present invention will now be described immunosensor 44 shown in FIGS. 8 & 9 includes first insulating substrate 45, first electrode 47, second electrode 48, insulator material 49, second insulating substrate 46, cutout portion 50, and window 51, which are all similar in composition and function to first insulating substrate 29, first electrode 31, second electrode 32, insulator material 33, second insulating substrate 30, cutout portion 34, and window 35 described above in FIGS. 6 & 7. (A two-electrode electrocell, utilizing working and reference electrodes, and a three-electrode electrocell are also possible, as described above for electrocell 19 and immunosensor 28.)

Figure 8:
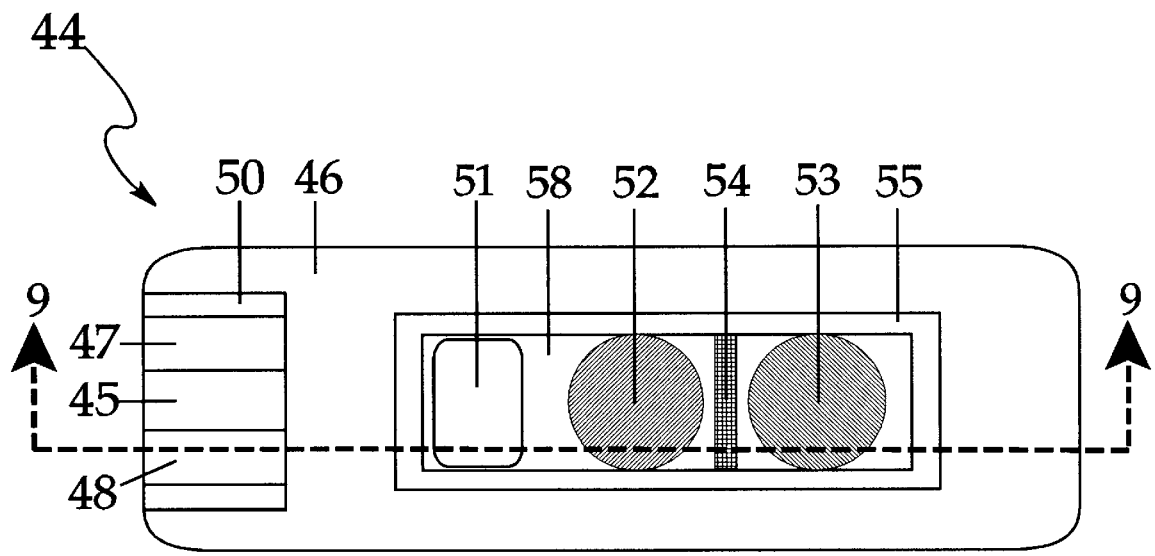
FIG. 8 is a schematic top view of an embodiment of an immunosensor of the present invention, excluding the fourth insulating substrate.
Figure 9:
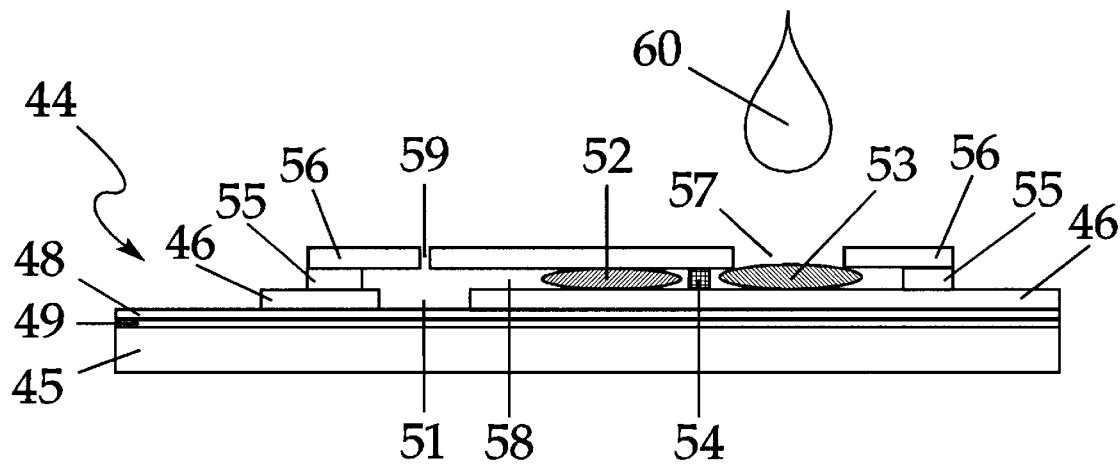
FIG. 9 is a schematic cross-sectional view of FIG. 8 taken along line 9—9 of FIG. 8, including the fourth insulating substrate.

About 5 μL of ED reagent 52 and 6 μL of EA reagent 53 are dispensed directly onto second insulating substrate 46 as shown in FIGS. 8 & 9. ED reagent 52 and EA reagent 53 are made as described above, dispensed onto second insulating substrate 46, then dried by heating at about 50° C. for about 15 minutes. Second insulating substrate 46 also has polymer 54, placed between ED reagent 52 and EA reagent 53. Polymer 54 can be any water-soluble polymer, such as polyvinyl pyridine, polyvinyl pyrrolidone, or polyvinyl imidazole, and preferably should be non-electroactive and non-reactive.

Third insulating substrate 55 is placed over second insulating substrate 46. Third insulating substrate 55 is a thin insulating substrate which preferably has adhesive material on each side to hold it in place. Third insulating substrate 55 includes cutout portion 58. Fourth insulating substrate 56 (not shown in FIG. 8) is placed over third insulating substrate 55, such that capillary space is formed within cutout portion 58 of third insulating substrate 55 which allows capillary flow from EA reagent 53 to ED reagent 52. Fourth insulating substrate 56 is about 250 microns thick, made of polyester, and includes sample window 57 (not, shown in FIG. 8) which exposes EA reagent 53, and vent hole 59 (not shown in FIG. 8).

Immunosensor 44 may be used to determine the concentration of an analyte in a whole blood sample by the following method. Whole blood sample 60 (about 20 μl) is applied to sample window 57 of immunosensor 44. A mixture of EA reagent 53 and blood sample 60 is formed. Polymer 54 allows whole blood sample 60 and EA reagent 53 to mix and react for a predetermined period of time, during which time polymer 54 is dissolved. After polymer 54 has dissolved, the solution of whole blood sample 60, EA reagent 53 and polymer 54 then flows to ED reagent 52 to complete mixing the immunoassay reaction components. The EA reagent 53, ED reagent 52, polymer 54, and blood sample 60 mixture is then drawn by capillary action (caused by cutout portion 58 and vent hole 59 ) to window 51 and settles on electrodes 47 and 48. After an incubation period of about 20 minutes, a potential difference of 450 mV is applied between electrodes 47 and 48 (palladium first and second electrodes, as described above, electrically connected to a power source and a current measuring meter). The current generated is measured for about 5 seconds. The amount of current measured 3 seconds after application of the potential difference is then compared to a calibration curve and analyte concentration in the whole blood sample is determined.

The meter and power source described above for use with electrocell 19 and immunosensors 28 and 44 will normally be adapted to apply an algorithm to the current measurement, whereby the presence or concentration of analyte is provided and visually displayed. Improvements in such a power source, meter, and biosensor system are the subject of commonly assigned U.S. Pat. No. 4,963,814 (issued Oct. 16, 1990), U.S. Pat. No. 4,999,632 (issued Mar. 12, 1991), U.S. Pat. No. 4,999,582 (issued Mar. 12, 1991), U.S. Pat. No. 5,243,516 (issued Sep. 7, 1993), U.S. Pat. No. 5,352,351 (issued Oct. 4, 1994), U.S. Pat. No. 5,366,609 (issued Nov. 22, 1994), White et al., U.S. Pat. No. 5,405,511, issued Apr. 11, 1995, and White et. al., U.S. Pat. No. 5,438,271, issued Aug. 1, 1995, the disclosures of which are hereby incorporated by reference.

EXAMPLE 4

Ferritin Assay

The Theophylline System Pack described above in Example 1 may also be modified as described below in order to perform an assay for ferritin according to the present invention.

In the ED reagent, goat antibody to ferritin coupled to ED is used at 0.4 nanomolar (nM) concentration in place of the theophylline-ED conjugate. The goat antibody may be coupled to ED through any number of standard techniques for protein crosslinking. For example, the goat antibody may be reacted with maleimide hexyl succinimide (MHS) to supply maleimide groups, and the ED is coupled to the activated goat antibody through the cysteine residues present. The product is then purified with gel filtration chromatography. (See, for example, "Chemistry of Protein Conjugation", Shan W. Wong, CRC Press.) In the EA reagent, mouse monoclonal antibody to ferritin is used at a concentration of 187 $\mu$g/ml in place of the mouse monoclonal antibody to theophylline. The ED and EA buffers remain the same, since they contain no theophylline-specific components.

A ferritin assay may be carried out as follows. 20 ml of ED buffer is added to the lyophilized ED reagent and allowed to dissolve (solution 1). 16 ml of EA buffer is added to lyophilized EA reagent and allowed to dissolve (solution 2). 35 $\mu$l of a sample containing ferritin is mixed with 100 $\mu$l of solution 1. This mixture is incubated for 12 minutes. 80 $\mu$l of solution 2 is then added to the mixture. The mixture is then allowed to incubate an additional 4 minutes. A 20 $\mu$l sample of this mixture is then applied to an electrochemical cell and a measurement made as described above. The current measured is then related to the concentration of ferritin in the sample through calibration standards. In this assay, the amount of current measured is inversely proportional to the amount of ferritin in the sample.

EXAMPLE 5 hCG Assay

The Theophylline System Pack described above in Example 1 may also be modified as described below in order to perform an assay for hCG according to the present invention.

The ED reagent contains the non-specific components listed above in Example 1. Antibody to hCG coupled to ED is used at 3.2 nM in place of the theophylline-ED conjugate. Goat antibody to biotin is also included at a concentration of 80 $\mu$g/ml. The EA reagent also contains the non-theophylline-specific components listed in Example 1, plus donkey antiserum to goat antibodies (added after a 13-fold dilution of the heat-treated serum). The ED and EA buffers remain the same as shown in Example 1. The hCG assay also requires a capture reagent which includes hCG conjugated to biotin. This conjugate may be prepared by standard techniques for coupling haptens to proteins (e.g., adding biotin-NHS ester (Pierce) dissolved in DMF to a solution of hCG in carbonate buffer, pH 9.0, incubating 1 hour, and removing unreacted biotin by gel filtration with a PD-10 column (Pharmacia). The capture reagent, contains the hCG biotin dissolved at 35 nM in EA buffer.

An hCG assay may be carried out as follows. 20 ml of ED buffer is added to the lyophilized ED reagent and allowed to dissolve (solution 1). 16 ml of EA buffer is added to lyophilized EA reagent and allowed to dissolve (solution 2). 35 $\mu$l of a sample containing hCG is mixed with 50 $\mu$l of solution 1 and incubated for 5 minutes. 75 $\mu$l capture reagent is then added, followed by an additional 5 minute incubation. 105 $\mu$l solution 2 is then added to the mixture and incubated for an additional 2.5 minutes. About 20 $\mu$l of the reaction mixture is then applied to an electrochemical cell and a measurement made as described above. The current measured is related to the sample hCG concentration through a standard curve. In this assay the current measured is directly proportional to the hCG concentration in the sample.

EXAMPLE 6

Vitamin $B_{12}$ Assay

The $B_{12}$ CEDIA® assay, commercially available from Boehringer Mannheim Corporation, may be modified as described below in order to perform an assay for $B_{12}$ according to the present invention. The modification to the $B_{12}$ CEDIA® assay would be carried out in a similar manner to the Theophylline System Pack modification described above in Example 1.

The ED reagent, which contains ED conjugated to cyanocobolamine ($B_{12}$ analog), is modified by using an electrochemically labeled substrate in place of the colorimetically labeled substrate provided in the commercial kit. The EA reagent, ED and EA buffers, pre-treatment reagent, and binding protein reagent remain unchanged from the commercial kit.

A $B_{12}$ assay may be carried out as follows. ED reagent is reconstituted with 15 ml ED buffer to form solution 1. EA reagent is reconstituted with 15 ml EA buffer to form solution 2. The binding protein reagent is reconstituted with 17 ml ED buffer. 48 $\mu$l of a sample containing $B_{12}$ is mixed with 57 $\mu$l of pre-treatment reagent and incubated 80 seconds. 125 μl of the binding protein reagent is added and incubated an additional 215 seconds. 100 μl of solution 1 is added and incubated an additional 375 seconds. 100 μl of solution 2 is added and incubated an additional 590 seconds. About 20 μl is then removed from the reaction mixture and placed in an electrochemical cell and a measurement made as described above. The current measured is related to the sample $B_{12}$ concentration through a standard curve.

EXAMPLE 7

Folate Assay

The folate CEDIA® assay, commercially available from Boehringer Mannheim Corporation, may be modified as described below in order to perform an assay for folate according to the present invention. The modification to the folate CEDIA® assay would be carried out in a similar manner to the Theophylline System Pack modification described above in Example 1.

The ED reagent, which contains ED bound to pteroylglutamic acid, is modified by using an electrochemically labeled substrate in place of the colorimetically labeled substrate provided in the commercial kit. The EA reagent, ED and EA buffers, pre-treatment reagent, and folate binding protein are unmodified from the commercial kit.

A folate assay may be carried out as follows. ED reagent is reconstituted with 15 ml ED buffer to form solution 1. EA reagent is reconstituted with 15 ml EA buffer to form solution 2. The folate binding protein is reconstituted with 15 ml ED buffer to form a binding protein solution. 42 μl of a sample containing folate is added to 42 μl of pre-treatment reagent and incubated 80 seconds. 100 μl of the binding protein solution is added and incubated an additional 215 seconds. 100 μl of solution 1 is added and incubated an additional 395 seconds. 100 μl of solution 2 is added and incubated an additional 590 seconds. About 20 μl is then removed from the reaction mixture and placed in an electrochemical cell and a measurement made as described above. The current measured is related to the sample $B_{12}$ concentration through a standard curve.

The present invention has been disclosed in the above teachings and drawings with sufficient clarity and conciseness to enable one skilled in the art to make and use the invention, to know the best mode for carrying out the invention, and to distinguish it from other inventions and from what is old. Many variations and obvious adaptations of the invention will readily come to mind, and these are intended to be contained within the scope of the invention as claimed below.

What is claimed is:

1. A diagnostic kit for determining the presence or concentration of an analyte in a fluid sample, comprising:
   (a) an enzyme donor reagent which comprises
      1) an enzyme donor polypeptide conjugate; and
      2) a labeled substrate, comprising an enzyme substrate cleavably linked to an electroactive label;
   (b) an enzyme acceptor reagent which comprises
      1) an enzyme acceptor polypeptide capable of combining with the enzyme donor polypeptide conjugate to form an active enzyme complex capable of catalyzing the cleavage of the electroactive label from the enzyme substrate; and
      2) a first antibody capable of immunologically, competitively binding to the analyte and the enzyme donor polypeptide conjugate and hindering formation of the active enzyme complex when bound to the enzyme donor polypeptide conjugate; and
   (c) an electrochemical immunosensor.

2. The diagnostic kit of claim 1, wherein the enzyme donor polypeptide conjugate is a conjugate of an enzyme donor polypeptide and at least one of an analyte or an analyte analog.

3. The diagnostic kit of claim 2, wherein the enzyme acceptor reagent further comprises an amount of the analyte sufficient to ensure that changes in concentration of the analyte in the fluid sample are substantially linearly related to changes in the current measured by an electrochemical measurement.

4. The diagnostic kit of claim 3, wherein the enzyme donor reagent further comprises an amount of added peptides, protein fragments, or proteins sufficient to reduce hydrolysis of the enzyme donor polypeptide conjugate from proteases in the fluid sample.

5. The diagnostic kit of claim 2, wherein the enzyme acceptor reagent further comprises a second antibody capable of immunologically binding to the first antibody, thereby further hindering formation of the active enzyme complex when the first antibody is bound to the enzyme donor polypeptide conjugate.

6. The diagnostic kit of claim 1, wherein the electrochemical immunosensor includes a first insulating substrate, first and second electrodes affixed to the first insulating substrate, and a second insulating substrate, which overlays the first and second electrodes has a window for exposing at least a portion of the first and second electrodes, and has a cutout portion at one end to allow contact between the electrodes and a meter and a power source.

7. The diagnostic kit of claim 6, wherein the first electrode is a working electrode and the second electrode is a counter electrode.

8. The diagnostic kit of claim 7, wherein the working and counter electrodes are palladium, platinum, gold, silver, titanium, copper, or carbon.

9. The diagnostic kit of claim 6, wherein the first electrode is a working electrode and the second electrode is a reference electrode.

10. The diagnostic kit of claim 1, wherein the enzyme substrate comprises μ-D-galactopyranoside and the electroactive label comprises 4-(1,4,7,10-tetraoxadecyl)-1-naphthyl, 4-methoxy-1-naphthyl, p-aminophenyl, p-nitrophenyl, chlorophenol red, o-nitrophenyl, umbelliferyl, o-methoxy-p-nitrophenyl, 3,4 dinitrophenyl, m-cyano-p-nitrophenyl, 4-nitrosalicylaldehyde, or 4-methyl-umelliferyl.

11. An electrochemical immunoassay method for determining the presence or concentration of an analyte in a fluid sample, comprising:
   (a) preparing a mixture which includes;
      (1) the fluid sample;
      (2) an enzyme donor reagent, which comprises:
         (i) an enzyme donor polypeptide conjugate; and
         (ii) a labeled substrate, comprising an enzyme substrate cleavably linked to an electroactive label; and
      (3) an enzyme acceptor reagent, which comprises (i) an enzyme acceptor polypeptide capable of combining with the enzyme donor polypeptide conjugate to form an active enzyme complex capable of catalyzing the cleavage of the electroactive label from the enzyme substrate; and (ii) a first antibody capable of immunologically, competitively binding to the analyte and the enzyme donor polypeptide conjugate and hindering formation of the active enzyme complex when bound to the enzyme donor polypeptide conjugate;

(b) applying the mixture to an electrochemical cell having first and second electrodes;

(c) applying, after incubation of the mixture, a potential difference between the first and second electrodes sufficient to oxidize the electroactive label that has been cleaved from the enzyme substrate, thereby generating a current; and (d) measuring the current and correlating the current to the presence or concentration of the analyte.

12. The electrochemical immunoassay method of claim 11, wherein the enzyme substrate comprises β-D-galactopyranoside and the electroactive label comprises 4-(1,4,7,10-tetraoxadecyl)-1-naphthyl, 4-methoxy-1-naphthyl, p-aminophenyl, p-nitrophenyl, chlorophenol red, o-nitrophenyl, umbelliferyl, o-methoxy-p-nitrophenyl, 3,4 dinitrophenyl, m-cyano-p-nitrophenyl, 4-nitrosalicylaldehyde, or 4-methyl-umelliferyl.

13. The electrochemical immunoassay method of claim 11, wherein the enzyme donor polypeptide conjugate is a conjugate of an enzyme donor polypeptide and at least one of an analyte or an analyte analogy.

14. The electrochemical immunoassay method of claim 13, wherein the enzyme acceptor reagent further comprises a second antibody capable of immunologically binding to the first antibody, thereby further hindering formation of the active enzyme complex when the first antibody is bound to the enzyme donor polypeptide conjugate.

15. The electrochemical immunoassay method of claim 13, wherein the enzyme acceptor reagent further comprises an amount of the analyte sufficient to ensure that changes in concentration of the analyte in the fluid sample are substantially linearly related to changes in the current measured by an electrochemical measurement.

16. The electrochemical immunoassay method of claim 15, wherein the enzyme donor reagent further comprises an amount of added peptides, protein fragments, or proteins sufficient to reduce hydrolysis of the enzyme donor polypeptide conjugate from proteases in the fluid sample.

17. The electrochemical immunoassay method of claim 16, wherein the electrochemical cell comprises a first insulating substrate, first and second electrodes affixed to the first insulating substrate, and a second insulating substrate, which overlays the first and second electrodes, has a window for exposing at least a portion of the first and second electrodes, and has a cutout portion at one end to allow contact between the electrodes and a meter and a power source.

18. The electrochemical immunoassay method of claim 17, wherein the first electrode is a working electrode and the second electrode is a reference electrode.

19. The electrochemical immunoassay method of claim 17, wherein the first electrode is a working electrode and the second electrode is a counter electrode.

20. The electrochemical immunoassay method of claim 19, wherein the working and counter electrodes are palladium, platinum, gold, silver, titanium, copper, or carbon.

21. An immunosensor useful for an electrochemical immunoassay of an analyte in a fluid sample, comprising:

(a) a first insulating substrate;

(b) first and second electrodes affixed to the first insulating substrate;

(c) a second insulating substrate, which overlays the first and second electrodes, has a window for exposing at least a portion of the first and second electrodes, and has a cutout portion at one end to allow contact between the electrodes and a meter and a power source;

(d) a porous substrate, which is impregnated with an enzyme donor reagent, overlays the window, and is spatially displaced from the working and counter electrodes, the enzyme donor reagent including:

(1) an enzyme donor polypeptide conjugate; and (2) a labeled substrate, comprising an enzyme substrate cleavably linked to an electroactive label;

(e) an enzyme acceptor reagent, which is placed on the second insulating substrate, the enzyme acceptor reagent including: (1) an enzyme acceptor polypeptide capable of combining with the enzyme donor polypeptide conjugate to form an active enzyme complex capable of catalyzing the cleavage of the electroactive label from the enzyme substrate; and (2) an antibody capable of immunologically, competitively binding to the analyte and the enzyme donor polypeptide conjugate and hindering formation of the active enzyme complex when bound to the enzyme donor polypeptide conjugate;

(f) a third insulating substrate, which overlays the second insulating substrate and has a cutout portion for exposing the enzyme donor reagent, the enzyme acceptor reagent, and the window in the second insulating substrate; and (g) a fourth insulating substrate, which overlays the third insulating substrate such that a capillary space is formed within the cutout portion of the third insulating substrate, has a window for exposing a portion of the enzyme acceptor reagent, and has a vent hole.

22. The immunosensor of claim 21, wherein the first electrode is a working electrode and the second electrode is a reference electrode.

23. Thee immunosensor of claim 21, wherein the enzyme substrate comprises β-D-galactopyranoside and the electroactive label comprises 4-(1,4,7,10-tetraoxadecyl)-1-naphthyl, 4-methoxy-1-naphthyl, p-aminophenyl, p-nitrophenyl, chlorophenol red, o-nitrophenyl, umbelliferyl, o-methoxy-p-nitrophenyl, 3,4 dinitrophenyl, m-cyano-p-nitrophenyl, 4-nitrosalicylaldehyde, or 4-methyl-umelliferyl.

24. The immunosensor of claim 21, wherein the first electrode is a working electrode and the second electrode is a counter electrode.

25. The immunosensor of claim 24, wherein the working and counter electrodes are palladium, platinum, gold, silver, titanium, copper, or carbon.

26. The immunosensor of claim 25, wherein the working and counter electrodes are made of the same material and are substantially the same size.

27. The immunosensor of claim 26, further comprising the power source in electrical connection with the working and counter electrodes and capable of supplying an electrical potential difference between the working and counter electrodes sufficient to cause electrooxidation of the reduced form of the label at the surface of the working electrode, and the meter in electrical connection with the working and counter electrodes and capable of measuring the current produced by the oxidation of the reduced form of the label at the surface of the working electrode.

28. An immunosensor useful for an electrochemical immunoassay of an analyte in a fluid sample, comprising:

(a) a first insulating substrate;

(b) first and second electrodes affixed to the first insulating substrate;

(c) a second insulating substrate, which overlays the first and second electrodes, has a window for exposing at least a portion of the first and second electrodes, and has a cutout portion at one end to allow contact between the electrodes and a meter and a power source;

(d) an enzyme donor reagent which is placed on the second insulating substrate, the enzyme donor reagent including
   (1) an enzyme donor polypeptide conjugate; and
   (2) a labeled substrate, comprising an enzyme substrate cleavably linked to an electroactive label;

(e) an enzyme acceptor reagent, which is placed on the second insulating substrate, the enzyme acceptor reagent including (1) an enzyme acceptor polypeptide capable of combining with the enzyme donor polypeptide conjugate to form an active enzyme complex capable of catalyzing the cleavage of the electroactive label from the enzyme substrate; and (f) an antibody capable of immunologically, competitively binding to the analyte and the enzyme donor polypeptide conjugate and hindering formation of the active enzyme complex when bound to the enzyme donor polypeptide conjugate;

(g) a polymer, which is placed on the second insulating substrate between the enzyme acceptor reagent and the enzyme donor reagent;

(h) a third insulating substrate, which overlays the second insulating substrate and has a cutout portion for exposing the enzyme donor reagent, the enzyme acceptor reagent, the polymer, and the window in the second insulating substrate; and (i) a fourth insulating substrate, which overlays the third insulating substrate such that a capillary space is formed within the cutout portion of the third insulating substrate, has a window for exposing a portion of the enzyme acceptor reagent, and has a vent hole.

29. The immunosensor of claim 28, wherein the first electrode is a working electrode and the second electrode is a counter electrode.

30. The immunosensor of claim 28, wherein the first electrode is a working electrode and the second electrode is a reference electrode.

31. The immunosensor of claim 28, wherein the enzyme substrate comprises β-D-galactopyranoside and the electroactive label comprises 4-(1,4,7,10-tetraoxadecyl)-1-naphthyl, 4-methoxy-1-naphthyl, p-aminophenyl, p-nitrophenyl, chlorophenol red, o-nitrophenyl, umbelliferyl, o-methoxy-p-nitrophenyl, 3,4 dinitrophenyl, m-cyano-p-nitrophenyl, 4-nitrosalicylaldehyde, or 4-methyl-umbelliferyl.

* * * * *

UNITED STATES PATENT AND TRADEMARK OFFICE
CERTIFICATE OF CORRECTION

PATENT NO. : 6,110,696
DATED : August 29, 2000
INVENTOR(S) : Mary E. Brown, et al.

It is certified that error appears in the above-identified patent and that said Letters Patent are hereby corrected as shown below:

On Page 1, change "Assignees: " to read as follows: -- Roche Diagnostics Corporation, Indianapolis, Indiana; Roche Diagnostics GmbH, Germany--.

Signed and Sealed this

Twenty-ninth Day of May, 2001

Attest:

NICHOLAS P. GODICI

Attesting Officer

Acting Director of the United States Patent and Trademark Office